United States Patent [19]

Hirschfeld

[11] Patent Number: 4,577,109
[45] Date of Patent: Mar. 18, 1986

[54] REMOTE MULTI-POSITION INFORMATION GATHERING SYSTEM AND METHOD

[75] Inventor: Tomas B. Hirschfeld, Livermore, Calif.

[73] Assignee: Regents of the University of California, Berkeley, Calif.

[21] Appl. No.: 445,619

[22] Filed: Nov. 30, 1982

Related U.S. Application Data

[63] Continuation-in-part of Ser. No. 194,684, Oct. 6, 1980.

[51] Int. Cl.[4] .................................. G01N 21/64
[52] U.S. Cl. ............................................ 250/461.1
[58] Field of Search .................. 356/32, 39, 44, 317, 356/318; 250/354, 461 R, 461 B, 231 R, 231 P; 350/96.18; 128/634

[56] References Cited

U.S. PATENT DOCUMENTS

| | | | |
|---|---|---|---|
| 3,591,810 | 7/1971 | Jackson . | |
| 3,724,383 | 4/1973 | Gallaghan et al. | 350/96.18 |
| 3,992,631 | 11/1976 | Harte | 250/461 B |
| 4,136,566 | 1/1979 | Christensen | 73/356 |
| 4,179,927 | 12/1979 | Saaski | 73/350 |
| 4,200,110 | 4/1980 | Peterson et al. | 356/412 |
| 4,304,461 | 12/1981 | Stewart et al. | 350/96.18 |
| 4,344,438 | 8/1982 | Schultz | 128/634 |
| 4,476,870 | 10/1984 | Peterson et al. | 250/458.1 |

FOREIGN PATENT DOCUMENTS

WO79/00377 6/1979 PCT Int'l Appl. .............. 250/227

Primary Examiner—Janice A. Howell
Attorney, Agent, or Firm—Stephen C. Macevicz

[57] ABSTRACT

A technique for gathering specific information from various remote locations, especially fluorimetric information characteristic of particular materials at the various locations is disclosed herein. This technique uses a single source of light disposed at still a different, central location and an overall optical network including an arrangement of optical fibers cooperating with the light source for directing individual light beams into the different information bearing locations. The incoming light beams result in corresponding displays of light, e.g., fluorescent light, containing the information to be obtained. The optical network cooperates with these light displays at the various locations for directing on-going light beams containing the same information as their cooperating displays from these locations to the central location. Each of these outgoing beams is applied to a detection arrangement, e.g., a fluorescence spectroscope, for retrieving the information contained thereby.

6 Claims, 14 Drawing Figures

REMOTE MULTI-POSITION INFORMATION GATHERING SYSTEM AND METHOD

CROSS-REFERENCE TO RELATED APPLICATION

This application is a continuation-in-part of U.S. application Ser. No. 194,684 filed Oct. 6, 1980.

BACKGROUND OF THE INVENTION

Field of the Invention

The present invention relates generally to techniques for gathering or obtaining information at one or more remote locations and, more particularly, to a specific technique for obtaining from one or more remote locations fluorimetric information, that is, fluorescent light emanating from and characteristic of particular materials at these locations, without utilizing entirely separate information gathering apparatus located at each of the information bearing locations.

Analytical monitoring and control are crucial in a variety of situations arising in medicine, industrial operations, and scientific research. However, in many cases, analysis or information gathering must take place at a distance because the region to be monitored is inaccessible or involves hazardous components, such as high pressures, high temperatures, corrosive materials, high radiation levels, or the like. The need to monitor critical parameters under such conditions arises in direct monitoring of blood parameters, such as $pO_2$, $pCO_2$, and pH; in monitoring nuclear reactor vessel parameters, such as temperature, pressure, and in the case of pressurized water reactors or boilers in general, the presence and concentration of certain corrosive ions in the coolant; in monitoring containment of hazardous materials at underground nuclear waste-disposal sites, or chemical dumping sites; in monitoring the quality of ground water; in monitoring reaction conditions at the working zone of a coal-liquification reactor; in monitoring acidity and selected ion concentrations in ore-tailing dumps undergoing microbiological leaching; or in monitoring parameters in like environments which are too hostile or inaccessible for most in situ analytical devices.

In medicine, invasive, or direct, monitoring of blood acid-base parameters and other selected ions is desirable, and in many cases necessary, in the management of critically ill patients or those undergoing complex surgical procedures. In particular, blood pH is regulated within very narrow bounds in normal individuals, varying no more than several hundredth of a pH unit from an average of 7.40. The pH is directly dependent on bicarbonate and dissolved $CO_2$ concentrations in the blood. As a consequence, several anesthetic agents and diseases affect blood pH, either directly or indirectly. In particular, diabetic acidosis which arises from depletion of serum bicarbonate, and pulmonary disorders and anesthetic agents which affect respiration can cause rapidly increased blood $pCO_2$, which in turn can produce striking alterations in blood pH. Either of these events are life threatening. Thus, there is an important medical need for directly monitoring blood pH.

Currently, the most widespread methods for direct blood pH measurement, or direct blood electrolyte monitoring, involve the use of ion-selective electrodes. While such electrodes can provide rapid and accurate measurements, there are several disadvantages to their use. The familiar glass pH electrode does not readily lend itself to the construction of invasive devices. Although miniature glass electrodes have been mounted on flexible catheters, small glass electrodes are inherently fragile and therefore present serious risk to the patient. Indeed, most investigators of in vivo blood pH have not employed invasive electrodes, but rather have adopted the somewhat more cumbersome technique in which an arterial-venous shunt is constructed to allow blood flow past a rigidly mounted, mechanically protected glass electrode.

Electrical interference is a major problem with high-resistance microelectrodes such as glass electrodes. Low-resistance miniature electrodes are available, and can give satisfactory measurements in the presence of other electrical equipment, but these require that the amplifying and processing electronics be physically close to the electrodes. Thus, the capability for remote measurements is lost. The most common electrical interference occurs in the 50-60 Hz and radio frequency ranges. While such interference can be reduced by special filtering electronics, both forms of interference can cause DC shifts which are easily overlooked.

Finally, the use of currently available electrodes can present direct hazards to patient safety. Electronically based transducers can pose an electrical hazard, especially when other such transducers are used at the same time, and polyvinyl chloride-based electrodes widely used with ionophores, such as valinomycin, can be dissolved by many gaseous anesthetics.

The electrical interference problem of electrodes is not limited to their uses in medicine. In any environment where high sensitivity is critical, electrical noise generated by extraneous fields will be a problem. Other problems inherent to the use of electrodes include the susceptibility of wire leads and couplings to deterioration under corrosive conditions, or conditions of alternating temperatures.

In the area of industrial process control a host of situations arise where chemical conditions, such as temperature, pressure, pH, redox potential, and ion concentrations, must be continously monitored. Any steam-based power system is susceptible to damage by pH levels which are too high or too low, or by water contaminated by corrosive substances, such as chloride ions, ferrous and ferric ions, copper, and dissolved gases, such as oxygen. Current techniques for monitoring levels of these materials are often indirect, and require that samples of feedwater be removed from the system. For example, water purity is frequently determined indirectly by the sodium tracer technique. In this technique a sample of feedwater is removed from the steam system, and its sodium content is analyzed by a flame photometer. The solids content of the feedwater is then inferred from the amount of sodium detected. Another technique involves measuring the electrical conductivity of the feedwater. Both techniques require that an expensive and complicated sampling system be maintained which is susceptible both to mechanical failure and to human error.

In the area of industrial microbiology, many processes require continous monitoring of chemical conditions. Microbiological leaching of low-grade ores is an area where a need exists for apparatus to remotely monitor parameters, such as oxygen concentration, ferrous and ferric ion concentrations, and pH. Commercial microbial recovery of copper and uranium is currently underway, and processes for recovering zinc, nickel, sulfur and cobalt using similar techniques are currently being considered. A major problem with current leaching processes is that they are carried out on a grand scale and are largely uncontrolled. For example, in a typical dump-leaching operation an entire valley is filled with low-grade ore tailings. As water percolates through the tailings insoluable minerals are made soluable by the action of certain bacteria, such as *Thiobacillus ferroxidans* and *Thiobacillus thiooxidans,* and are carried to the mouth of the valley where they are extracted.

The action of the commercially most important leaching bacteria is critically dependent on pH, ferrous and ferric ion concentrations and oxygen concentration. For effective use of such bacteria these parameters must be monitored and controlled. However, because of the lack of inexpensive and rugged sensors, extensive monitoring of large-scale leaching operations is not commercially feasible.

Many of the above-mentioned difficulties with current information-gathering technology can be overcome by using remote, in situ optical probes coupled to a detector by optical waveguides, or fiber optics. Fiber optics are durable, corrosion-resistant, heat-resistant, impervious to electrical or magnetic interference, and are available in very small diameters, which makes them amenable for use with miniature probes.

Peterson, et al., in U.S. Pat. No. 4,200,110, dated April 29, 1980, discloses a remote pH sensing device which employs an optical transducer connected to a detector by two fiber optics. The optical transducer is a membranous-walled chamber or a gel which contains a pH sensitive dye. The dye is illuminated with white light transmitted by one fiber optic, and the light scattered or emitted by the dye molecules is collected by the other fiber optic. Use of more than one fiber optic reduces sensitivity because precise alignment of the illuminating and light-collecting fibers must be maintained, and because illumination of dye molecules is less efficient when separate fibers for illumination and collection are used than if a single fiber is used for both collection and illumination.

Harte in U.S. Pat. No. 3,992,631, dated Nov. 16, 1976 discloses an apparatus for measuring fluorescent emissions from fluorochromes immobilized on a solid surface. The apparatus employs multistrand cables of fiber optics both to transmit an illumination beam and to collect fluorescent emissions. As with Peterson, et al., the sensitivity and reproducibility of Harte's apparatus is reduced by the use of separate fibers for illumination and collection. Also, for long range remote applications the cost of multistrand fiber optic cables can be prohibitive. Because of this its utility as an on-line process monitoring device is severely limited.

The foregoing illustrates some of the limitations of current process-monitoring technology. It is apparent that it would be advantageous to provide alternatives to available methods, particularly in regard to methods for remote, multiposition information gathering in hostile or inaccessible environments.

SUMMARY OF THE INVENTION

It is therefore one object of the present invention to provide an uncomplicated, reliable and yet economical technique for obtaining specific information from remote locations, especially hostile locations or at substantial distances (e.g. 1000 feet) where required and without requiring ruggedized instruments or equally rugged sampling systems at the measurement site.

A more particular object of the present invention is to provide a multi-location information gathering technique of the type just recited in which the primary instrumentation is common to all of the information bearing locations and all of these locations are interrogated in a substantially sequential manner.

Another particular object of the present invention is to provide a multi-location information gathering technique in which its primary instrumentation and the various information-bearing locations are interconnected optically so as to make the technique especially suitable for gathering information located in hostile environments.

Still another particular object of the present invention is to provide a multi-location information gathering technique wherein the various information-bearing locations are each connected to the same primary instrumentation by a single fiber optic.

A further particular object of the present invention is to provide an uncomplicated, reliable and yet economical technique for obtaining from a given location or substantially simultaneously from a number of given locations information in the form of measurements of fluorescent light emanating from and characteristic of particular material at the information bearing locations and also a technique which utilizes a single fluorescence spectroscope even though more than one information bearing location may be involved and even though these locations may be in relatively hostile environments.

Yet a further particular object of the present invention is to provide uncomplicated, reliable and yet economical light focusing and collecting devices for use in the technique last recited, while maintaining the normal signal gathering efficiency of fluorescence spectroscopy despite the severe optical constraints of interfacing to and transmitting the light through low attenuation fiber optic types.

Another particular object of the present invention is to provide a system and method for remote data sensing such as pH sensing at one or more locations in inaccessible or hostile environments.

Still another particular object of the present invention is to provide a method utilizing fiber optics for monitoring human or animal blood characteristics such as pH.

Another particular object of the present invention is to provide systems for remotely sensing concentrations of soluable chemical compounds, such as ferric ion concentrations, chloride ion concentrations, salt concentrations, or iodine concentrations in one or more locations and in hostile or inaccessible environments.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

As will be seen hereinafter, the overall information gathering technique disclosed herein is one which utilizes a single source of light provided at a location away from the information bearing location or locations. Means including an arrangement of optical fibers and the light source cooperate to direct individual beams of light into the various information bearing locations for causing the production of light signals which can be measured and which contain the information to be obtained at these latter locations. This "light signal" can be a result of fluoresence, light scattering, reflectance or other phenomena which causes light (both in the visible and invisible spectrum) to be re-emitted or produced as a result of the initiating beam. The optical means including its arrangement of fibers and coupling devices at the instrument as well as sampling devices at the distal end cooperate to direct outgoing beams of light towards locations to be measured, and return the remote signals to a central location, preferably the same location as the light source.

In the specific embodiments disclosed herein, the information to be obtained results from the fluorescence of specific material at each of the various information bearing locations. The incoming light beams are used at least in part to cause the material to fluoresce and a single fluorescence spectroscope serves to detect and retrieve the information contained in the return beams produced as a result of the sample fluorescence at the remote end.

The present invention is addressed to problems associated with remote, multi-position information gathering in hostile or inaccessible environments. It advantageously overcomes many of these problems by combining rugged, high quality fiber optics with simple in situ optical transducers for generating optical signals related to information at remote locations, such as concentrations, pressures, temperatures and the like. For medical and industrial pH and ion concentration measurements the problems of fragile, electrically-based pH and ion probes are overcome by the availability of small-diameter, catheter-sized communications-type fiber optics coupled with suitable pH-sensitive or ion-sensitive fluorescent probes. The information gathering system as taught in accordance with the present invention also advances the technology of industrial process monitoring (1) by increasing the sensitivity of measurements by employing optical means for transmitting information which are impervious to electrical or magnetic interference, (2) by reducing the cost of monitoring large-scale processes by obviating the need for separate analytical instrumentation for each sensor, and (3) by increasing the reproducibility of measurements between sensors by having all signals analyzed by the same instrument.

BRIEF DESCRIPTION OF THE DRAWINGS

Further objects of the invention, together with additional features contributing thereto and advantages accruing therefrom will be apparent from the following description of a preferred embodiment of the invention which is shown in the accompanying drawings, which are incorporated in and form a part of the Specification. In the drawings.

DETAILED DESCRIPTION OF THE INVENTION

Figure 1:
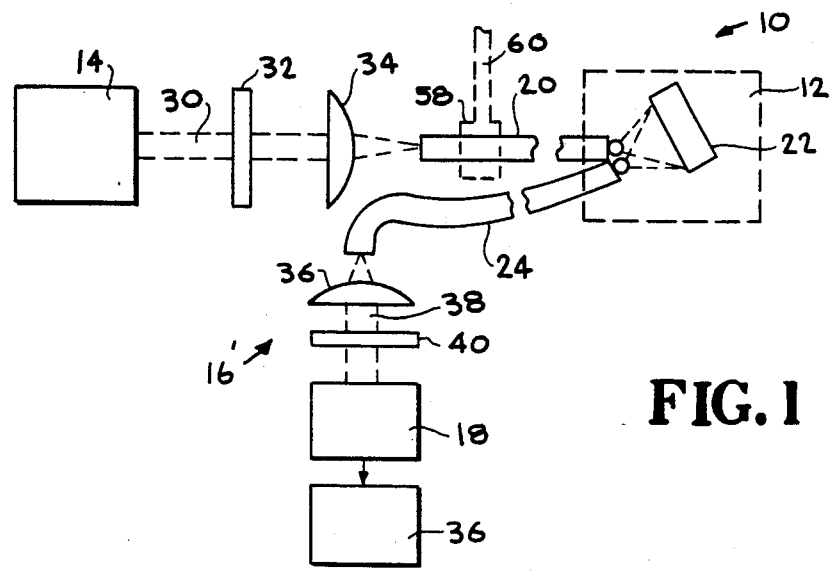
FIG. 1 diagrammatically illustrates a system for obtaining fluorimetric information from a single remote location in accordance with the present invention, using separate fibers for sending out the exciting light and receiving back the excited fluorescence, scattering, or reflectance signal.

Turning now to the drawings, attention is first directed to FIG. 1 which, as stated above, diagrammatically illustrates a system for obtaining specific fluorimetric information for a given location. The system is generally indicated at 10 and a particular information bearing location which may or may not be hostile environment of the type recited above is indicated by dotted lines at 12. As will be discussed in more detail below, system 10 includes a source of light 14, which must be capable of being focused efficiently to the small diameter and acceptance angle of a low attenuation communication fiber, an overall optical network 16 including an arrangement of communication grade (low attenuation) optical fibers, and a fluorescent spectroscope 18. Light from source 14 is converted into a beam which by means of the arrangement of optical fibers, for example a single fiber 20, directs the light beam into location 12 and onto a section of material 22 for causing the latter to fluoresce in a way which is characteristic of the material. Network 16 including its arrangement of optical fibers, for example a single fiber 24 comprising part of the arrangement, collects part of the fluorescent signal into a returning beam of light containing the same information as the fluorescence to spectroscope 18. While not shown in FIG. 1, the source of light 14 and spectroscope 18 are preferrably positioned at the same location. In addition, suitable data processing equipment 26 may be provided for acting on the information retrieved by the spectroscope 18 for subsequent processing purposes.

Referring now to the specific components making up overall system 10 in more detail, attention is first directed to light source 14. The light source may be of a suitable type which produces a beam of light 30 compatable with material 22 and fluorescent spectroscope 18, that is, a beam capable of causing material 22 to fluoresce in a way which is characteristic of the particular information to be sought from material 22. In a preferred embodiment, the light source is a laser apparatus and the beam 30 is monochromic light displaying a wavelength in the ultraviolet-visible-near infrared region.

The overall optical network 16 including its arrangement of optical fibers may be of any suitable type so long as it functions in the manner described above. In the embodiment illustrated in FIG. 1, this network includes an emission filter 32 and lens 34. The emission filter serves to eliminate laser cavity emission from the beam so as to confine the latter to a single wavelength. Lens 34 is appropriately located in beam 30 behind filter 32 and in front of one end of optical fiber 20 for focusing the beam onto the end of the optical fiber for transmission therethrough with minimum entry losses. The optical fiber itself is preferably one which is presently available in the communications industry for propagating a light beam, having a small cross-section, for example on the order of a few hundred microns, over many hundreds of yards with only slight attenuation. The specific optical fiber is one which can be readily purchased by designating it as the type used in the telephone system. For example, Valtec PC-10 fiber optics are suitable (Valtec Optical Group, Waltham, MA). Optical fiber 24 is preferably of the same type. In the embodiment illustrated, these two optical fibers form the entire arrangement of optical fibers comprising part of overall optical network 16. However, as will be discussed hereinafter, the optical fiber arrangement may be formed in a number of different ways.

Figure 2:
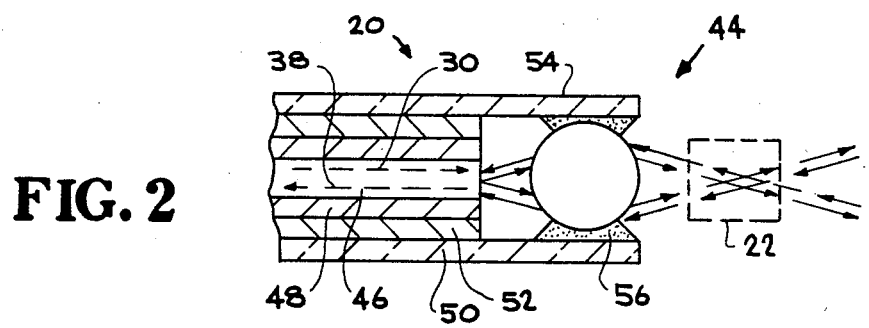
FIG. 2 is an enlarged axial sectional view illustrating one end section of an optical fiber which may be used with the system of the general type illustrated in FIG. 1 and a light focusing and gathering device designed for such a system.

In addition to emission filter 32, lens 34 and the two optical fibers just mentioned, overall optical network 16 includes a second lens 36, specifically a collector lens for capturing and straightening the outgoing beam generally indicated at 38, a wavelength filter 40 serving to filter out unwanted light from the beam. In addition to these components and those described above, overall optical network 16 includes suitable means cooperating with the end of optical fiber 20 at location 12 for focusing incoming beam 30 onto material 22 to produce fluorescence and suitable means cooperating with the adjacent end of optical fiber 24 for collecting light from the fluorescent display so as to form outgoing beam 38. Each of these latter means may be of any suitable type to be discussed below with respect to FIGS. 3A-3C. However, one such arrangement which can be used both as a focusing means and as a light collecting means is illustrated in FIG. 2 and generally designated by the reference numeral 44. As seen in this figure, arrangement 44 is in the form of spherical lens, specifically a saphire ball in a preferred embodiment. FIG. 2 also shows an end section of optical fiber 20 in detail. As seen there, this fiber includes a single light transmitting core at 46 concentrically disposed inside an outer cladding 48 which is bonded inside a glass tube 50 by means of suitable bonding cement 52 located concentrically therebetween. The outermost glass tube includes an end section 54 which extends beyond the central core and cladding material for fixedly supporting lens 44 in a concentrically disposed position by suitable bonding cement generally indicated at 56. As a focusing device, lens 44 acts as a collector for incoming beam 30 (indicated by dotted lines) on one side and focuses the collection light to a point at material 22 on its opposite side. As a collector, the lens collects the light resulting from the fluorescent display on one side and focuses its collected light onto the end of the core 46 on its opposite side to provide outgoing beam 38 (indicated by dotted lines).

Overall information gathering system 10 has been described above as having two optical fibers, incoming fiber 20 and outgoing fiber 24. It is, however, preferable to provide an arrangement of optical fibers in which one fiber is common to both the incoming beam and the outgoing beam. For example, incoming beam 30 could be directed into location 12 in the same manner as described above. However, instead of utilizing a second, separate optical fiber 24 and associated collector lens, the optical fiber 20 and its associated focusing lens 44 could be used to collect the light from the fluorescent signal as will be discussed in more detail below with respect to FIGS. 3A-3C. This collected light could be directed back into and through optical fiber 20 toward source 14. However, a suitable beam splitter, for example, those to be discussed specifically in FIGS. 3B and 3C (indicated by dotted lines at 58 in FIG. 1) would be provided for diverting this outgoing beam along a separate path defined by a separate optical fiber 60 which could otherwise be identical to previously recited optical fiber 24, but without a collector lens. The opposite end of this latter optical fiber would be coupled to lens 36 in the same manner as optical fiber 24. This overall configuration, of course, assumes that the outgoing beam of light is produced at a wavelength sufficiently different from the incoming beam so that the two can be separated.

Figure 3A:
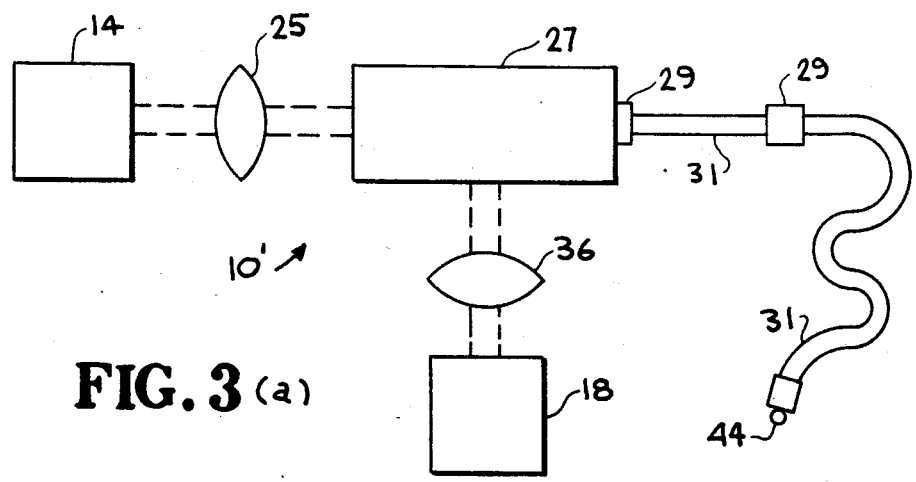
FIG. 3A diagrammatically illustrates a system similar to FIG. 1 but one which utilizes a common (single) optical fiber.

Having described system 10 and arrangement 44, attention is directed to a modified system 10' which requires only a single fiber for directing the beam of light to a remote control location and for collecting the resultant light signal thereat, as briefly discussed above. This latter system is illustrated in FIG. 3A and includes a light source capable of focusing on a very small spot, e.g., the laser 14 illustrated in FIG. 1 or possibly in ultra high pressure mercury arc lamp such as used in fluorescence microscopy. A beam from this source is acted on by an illuminator lens 25 and thereafter passes onto a single fiber bidirectional coupler 27. A readily provided fiber optics connector 29 serves to connect one end of a long distance communication optics fiber 31 to the coupler. The fiber's other end is connected to another fiber 31 by a similar connector 29. The distal end of the second fiber 31 includes an arrangement 44 as discussed in FIG. 2 or like arrangement serving both to illuminate the sample under test and for collecting the light signal resulting therefrom. This light signal is returned by the fibers 31 to coupler 27 which redirects the collected light beam through the collector lens 36 and thereafter to the fluorescent spectrometer 18.

Two examples of couplers (which also serve as beam splitters) are illustrated in FIGS. 3B and 3C generally and are designated by the reference numerals 27' and 27", respectively. The beam splitter 27' cooperates with the previously recited illuminator lens 25, connector 27 and collector lens 36 along with a dichroic beam splitter on an intensity splitting beam splitter. The former must be changed for each set of fluorescence excitation and emission wavelengths used while the latter one does not but does impose a heavy penalty in signal levels. The arrangement 27″ is a perforated mirror in order to geometrically separate the low convergence illumination beam (the incoming beam) and the more divergent return beam (which is limited only by the fiber numerical aperture).

Returning briefly to FIG. 2, attention is again directed to the combination beam focusing and collection arrangement 44. In describing this arrangement above, it was assumed that the material 22 being analyzed emits sufficient fluorescent light to provide a strong enough outgoing beam 38 to be analyzed. It was also assumed that there is a desire to collect all of the fluorescent light emitted by the material. In some cases, material 22 may not be of a type which by itself emits a strong enough fluorescent signal to be analyzed. In other cases, material 22 may include ingredients which fluoresce unwanted light. To eliminate these problems, lens 44 can be provided with an outer coating which combines with the incoming beam to cause the material 22 to give a fluorescent signal to a greater degree. For example, a solution of rubrene in polystyrene plastic coating could be provided when material 22 is iodine, which extinguishes the rubrene fluorescence. In any event, once material 22 is selected, the coating which will enhance fluorescence can be readily selected.

Figure 4:
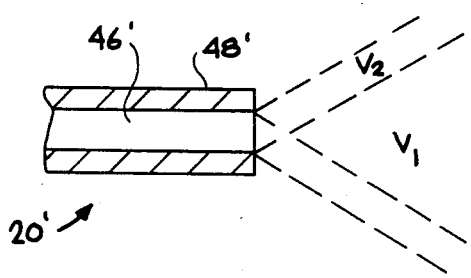
FIG. 4A diagrammatically illustrates the optical characteristics at the end of an optical fiber of the general type used in the systems of FIGS. 1 and 3A.
FIG. 4B is an enlarged axial view, in section, illustrating an end segment of an optical fiber which may be used with the systems of FIGS. 1 and 3A and a light focusing and gathering device for use with such systems and designed in accordance with the second embodiment.
FIG. 4C is a view similar to FIG. 4B (and FIG. 2) but illustrating still another embodiment of a light focusing and gathering device particularly suitable for the system shown in FIG. 3A.
FIG. 4D shows a porous glass plug attached to the end of a fiber optic.
FIG. 4E shows a porous glass capillary tube with a gel filling attached to the end of a fiber optic.
FIG. 4F shows a chamber with a membranous wall attached to the end of a fiber optic.
FIG. 4G shows a chamber with a membranous wall and and an associated reagent reservoir attached to the end of a fiber optic.
Figure 4:
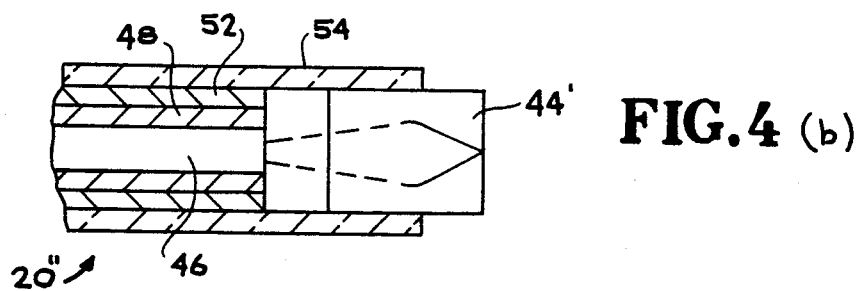
Figure 4:
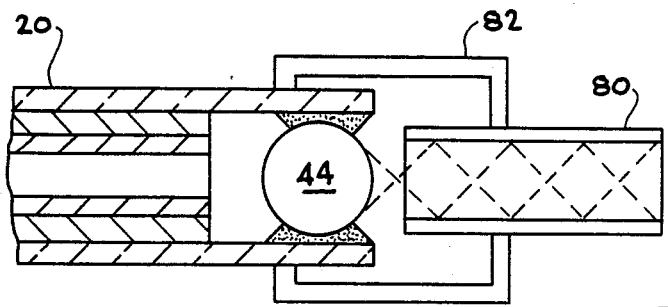
Figure 4:
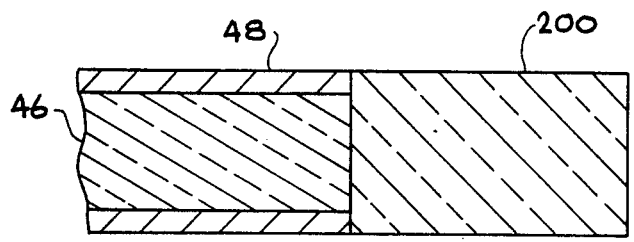
Figure 4:
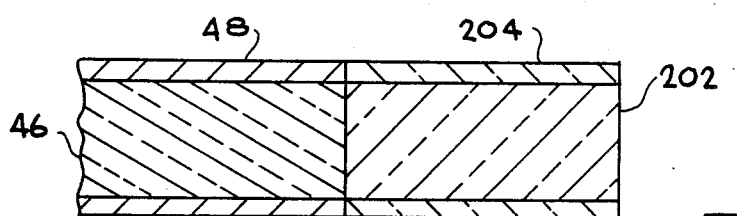
Figure 4:
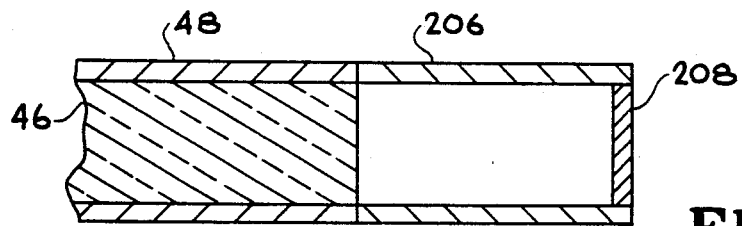
Figure 4:
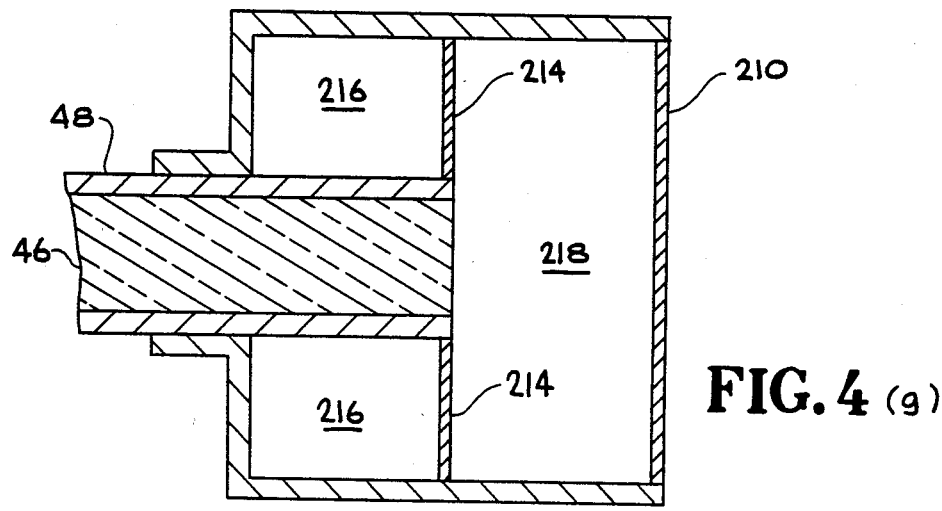

In order to more fully understand the way in which a single fiber can be used to direct a beam of light into a particular area under evaluation while at the same time serving to collect a resultant light signal therefrom and cause or aid in causing the production of a suitable light signal, attention is briefly directed to FIGS. 4A to 4C. FIG. 4A illustrates an optical fiber 20′ similar to previously described fiber 20 but without the outer surface 50. Rather as seen in FIG. 4A, fiber 20′ includes a fiber core 46′ and outer cladding 48′. FIG. 4A specifically illustrates the way in which the fiber 20′ distributes and collects light without the aid of arrangements such as the arrangement 44 illustrated in FIG. 2. In FIG. 4A, the possible light which might result at the end of the fiber can be divided into three groups, the central cone shaped group designated at V1, the larger cone shaped area described at V2 and the area V3 outside the larger cone shaped area. All of the light emitted backwards towards the fiber core from within the volume V1 will be collected by the fiber. On the other hand, only part of the light emitted backwards towards the fiber core from within the volume V2 (excluding the volume V1) will be collected by the fiber. Finally, none of the light within the area designated at V3 will be collected by the fiber. The converse of each of these results is equally true, that is, light from the fiber will illuminate the entire volume V1, only part of the volume V2 and none of the volume V3.

An arrangement such as that illustrated in FIG. 4A is equivalent to a sample cell 0.22–0.8 ×fiber diameter (in depth), for practical values of the fiber numerical aperture. In order to increase the light signal, larger fiber core diameters could be used but soon become too costly and unwieldy, since the low attenuation communication fibers are rather small. Lenses can, however, be used to increase the apparent fiber diameter, but should be high in index to avoid strong performance alterations produced by sample refractive index changes.

A much more practical embodiment to use for directing a beam of light into a given area and for collecting the resultant light signal is the previously described arrangement 44 illustrated in FIG. 2. However, when the sample is not fluorescent, or when its fluorescence is not selective enough to derive exclusively from the species being sought, specific fluorescent reagents, fluorescense extinction reagents or extraction reagents can be used. These will produce a fluorescent signal which is affected by the sample in a well-defined manner. Such reagents can readily be immobilized adjacent to the end face of the fiber core by means of a suitable emulsion, a gel, porous glass, membranous-walled chambers, or other suitable means for microencapsulation. Several such methods for immobilizing dye molecules are described in U.S. Pat. No. 4,200,110. The methods are directly applicable to immobilizing fluorescent extraction reagents and fluorescent extinction reagents. Accordingly, U.S. Pat. No. 4,200,110 is incorporated herein by reference. The fluorescent extraction and extinction reagents will be referred to as optical transducing means. For a lens system, the reagent location would have to be in and spaced in front of the lens, requiring a separate holder. To put it on the lens end face would be simpler, but to provide the focus there would require a lens index greater than two times the medium, which is extremely difficult given material limitations in the wavelength region discussed previously.

A different lens type, specifically the commercial selfor (Nippon Electric Company, Tokyo, Japan) rod lens, has a focus on its end surface, and can be used here to advantage. This lens is based on a rod with a parabolic radial distribution of refractive indices and a preselected length. Such a lens is illustrated in FIG. 4B at 44′ in combination with the fiber 20″ which is identical to previously illustrated fiber 20 and includes the same components including the same extended end. In this regard, note that the lens 44′ is fixedly contained in the extension 54 in spaced relationship with the fiber core itself indicated at 46. In this way, the reagent can be located on the flat end surface of the rod lens.

Classes of fluorescent extinction reagents and fluorescent extraction reagents are available for sensing some chemical parameters. In particular, a large number of fluorescent indicator molecules exist for determining pH. A list of several dozen is provided in the *CRC Handbook of Chemistry and Physics*, 55th Edition (1974). Accordingly, the list is incorporated herein by reference. Also, the Eastman Organic Chemical Company provides a large number of fluorescent pH indicator molecules applicable for use with the present invention. A fluorescent indicator molecule of particular interest for medical application is morin (Eastman Organic Chemical Company, Rochester, NY), which emits different intensities of green fluorescence over a pH range of 7.0–8.5.

Some applications may require that a wider pH range be monitored than can be accommodated by any single indicator molecule. In such cases several types of fluorescent indicators are employed wherein each type covers a separate pH range. Multiple indicator molecules are also necessary if certain constituents or contaminants of the sample solution are able to quench the emissions of one or more of the pH-sensitive molecules. Indicators are chosen so that at least one is impervious to the action of the quenching agent. Where multiple fluorescent indicator molecules are employed, it is sometimes necessary to illuminate the multiple types of molecules with light of more than one wavelength for optimal performance.

Similary multiple indicator molecules may be employed for detecting a plurality of different chemical species with a single sensor.

When immobilizing fluorescent indicator molecules in gels, in porous glass, or the like, high concentrations should be avoided in order to prevent concentration quenching. For example, for the indicator molecule fluorescein concentrations of less than 100 ppm should be used.

A hybrid method of immobilizing indicator molecules is provided by combining porous or sintered glass with a gel, such as acrylamide. Such a configuration combines the strength of the glass with the more versatile chemical properties of the gel. A capillary tube of porous glass with a gel filling, or a solid glass plug (either of sintered glass or of porous glass) impregnated with the gel are suitable means for immobilizing fluorescent indicator molecules. In either case the glass is fixed to the fiber optic by cement, a clamp, or the like. Porous glass is available in a variety of forms from Corning Glass Works Company under the trade name of Vycor "Thirsty" Glass. Such above-mentioned means for immobilizing fluorescent indicator molecules will be referred to as immobilization means.

FIG. 4D illustrates a fiber optic with a solid glass plug 200 attached to its end. The fiber core is 46, and the fiber cladding is 48. FIG. 4E illustrates a fiber optic with a porous glass capillary tube 204 attached to its end. In this embodiment the capillary tube is filled with a gel 202. FIG. 4F illustrates a fiber optic with a membranous-walled chamber attached to its end. The cylindrical body attached to the fiber optic is 206. It can be composed of any suitable impermeable solid, such as glass, stainless steel, or the like. One end of cylindrical body 206 is covered by membrane 208, which may be ion-selective or size-selective depending on particular applications.

Besides the above-mentioned organic indicator molecules, the inorganic uranyl ion is a sensitive indicator of pH over the range from 0 to about 6. The ion is immobilized by containing it in a membranous-walled chamber as shown in FIG. 4F which allows passage of the hydrogen ions but prevents escape of the uranyl ions. The term immobilization means will also be understood to include such membranous-walled chambers. The range over which uranyl is sensitive to pH could be especially useful in microbial leaching operations, as the bacteria involved in such operations are highly acidophilic.

Alternatively, pH is determined from uranyl fluorescence by providing a reservoir means, as shown by way of the example in FIG. 4G, wherein a reservoir of uranyl ion is contained in the toroid-shaped chamber, or reservoir, 216. Porous membrane 214 inhibits the diffusion of uranyl into the adjacent cylindrical chamber and porous membrane 210 inhibits the diffusion of uranyl out into the environment. The two membranes are chosen so that the uranyl concentration in the cylindrical chamber remains constant over interals of time short in comparison to the expected life of the uranyl reservoir. Thus, for a given reservoir size, initial uranyl conectration membrane types, and membrane surface areas of the uranyl concentration over the expected life of the reservoir is known. Given the uranyl concentration in the adjacent cylindrical chamber, pH is readily determined from its fluorescent intensity.

Uranyl fluorescence is effectively quenched by ferric ions. Thus, a ferric ion detector is obtained by sequestering a known quantity of uranyl ions in a membranous-walled chamber permeable to the ferric ions. The uranyl is maintained at a constant pH either by sequestering a known amount of polyphosphoric acid in the chamber, or by providing an acid reservoir near the chamber from which the acid can be bled into the chamber at a slow, constant rate. The object in either case is to maintain the uranyl ion in a low pH environment where maximum fluorescence occurs. The preferred acid is phosphoric, or polyphosphoric where no reservoir is used, although other acids, e.g. nitric, are suitable. Ferric ions can be detected by their reduction of uranyl fluorescent intensity or by their reduction of uranyl fluorescent lifetime. Although measuring fluorescent lifetime requires additional apparatus, it has two advantages over measuring fluorescent intensity for determining ferric ion concentrations. First, fluorescent lifetime is independent of illumination beam intensity. Thus, changes in illuminization beam intensity due to output variations or misalignment of optics will not effect concentration measurements. And second, the signal-to-noise ratio can be enhanced because of the relatively long-lived uranyl fluorescence. To measure fluorescent lifetime the uranyl ions are repetitively iluminated by interrupting the illumination beam with a mechanical chopper. While the illumination beam is interrupted uranyl fluorescent decay is observed. Since uranyl fluorescense is long-lived (up to 200 $\mu$sec in the absence of ferric ion quenching), it will be observed without background interference from other short-lived fluorescers. Thus, the signal-to-noise ratio is enhanced, at least for lower ferric ion concentration measurements.

As pointed out below the acid reservoir and membranous-walled chamber is also used as a means for diffusing uranyl ions (instead of acid) past the end of the fiber optic. In either case the chamber or means containing the material to be bled into the environment, e.g., the toroidal-shaped closed region in FIG. 4G, will be referred to as the reservoir means. In the case of FIG. 4G the reservoir means merely comprises a single chamber, the second membranous-walled chamber, connected to the adjacent cylindrical chamber, also referred to as the first membranous-walled chamber. The two chambers are connected by a common wall which is the annular-shaped membrane 214.

Alternatively, ferric ions concentractions can be determined by providing a reservoir as shown in FIG. 4G wherein the toroidal-shaped reservoir contains uranyl instead of acid. The adjacent cylindrical chamber contains a known amount of polyphosphoric acid. Membrane 210 is chosen so that is it permeable to ferric ions but impermeable to polyphosphoric acid. This embodiment has a limited life depending on the size of the uranyl reservoir. In both this embodiment and the pH-sensitive optical transducing means using uranyl the annular-shaped membrane 214 and disk-shaped membrane 210 are chosen to control the diffusion of the material in reservoir 216 to the environment.

Figure 6:
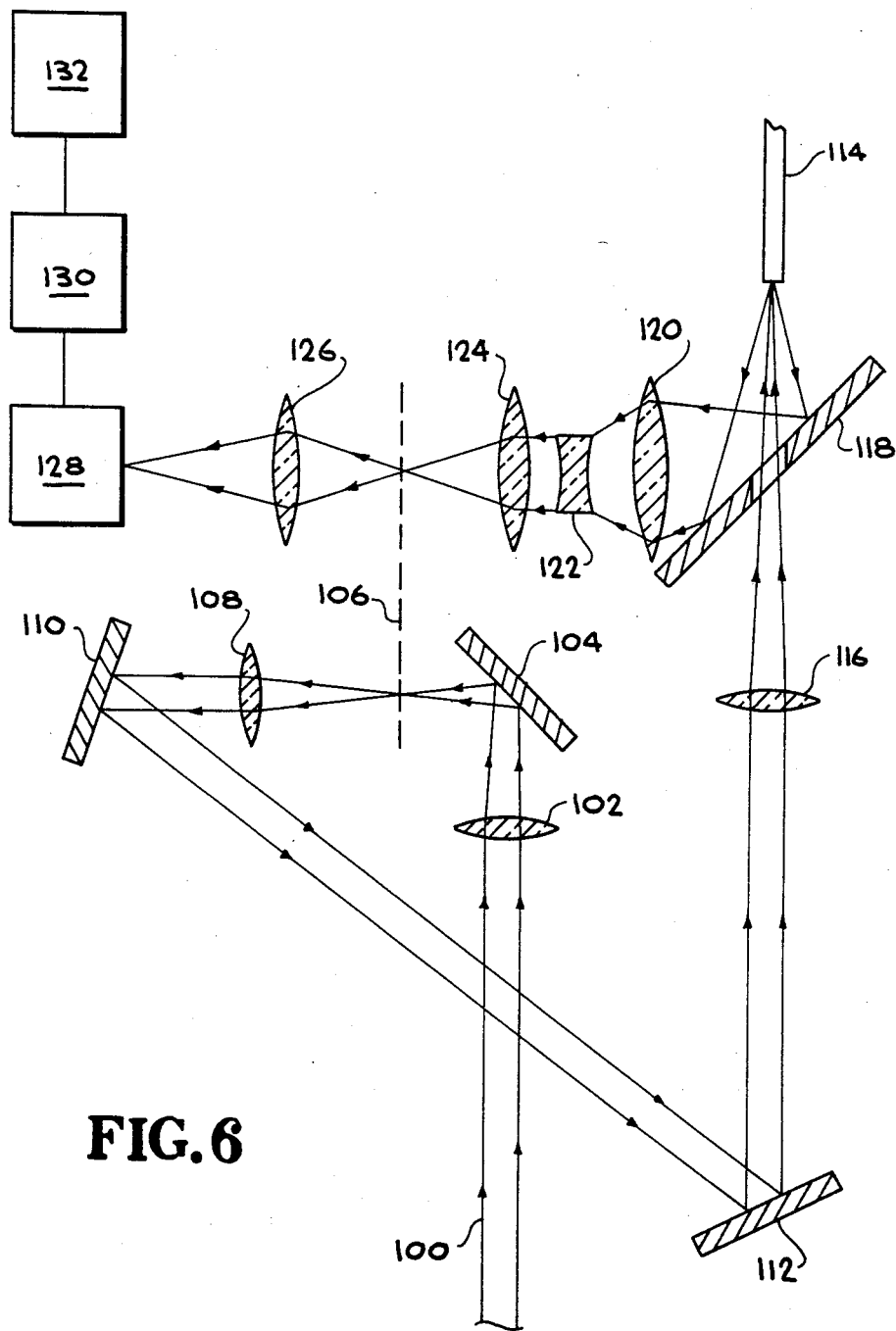
FIG. 6 illustrates an optical arrangement for measuring fluorescence lifetime of a fluorescent material at the sensing end of a fiber optic.

An optical arrangement incorporating a mechanical chopper suitable for measuring uranyl fluorescent lifetime is shown in FIG. 6. Laser input beam 100 is focused by lens 102 and deflected by mirror 104 so that the chopper blade 106 interrupts the beam at its focal point. The beam is then recollimated by lens 108 and deflected by mirrors 110 and 112 for injection into fiber optic 114. Lens 116 focuses the beam for injection. Light returning from sensing end of the fiber (i.e., the outgoing beam) is separated from the beam being injected (i.e., the incoming beam) by a beam splitting means 118, e.g., like the one illustrated in FIG. 3C. Light exiting the fiber and separted by the beam splitting means is collected, collimated and focused by lenses 120, 122 and 124, respectively. The focus of the beam is located in the path of the chopper blade. Lens 126 then focuses the beam to fluorescent spectrometer 128. A photomultiplier tube 130 converts the optical signal to an electrical one which is then processed by signal processing electronics 132.

FIG. 4G illustrates a fiber optic with an attached acid reservoir and membranous-walled chamber. The cylindrical body is 212 which fits on the end of a fiber optic (with core 46 and cladding 48). The cylindrical body 212 is divided into two closed regions by annular-shaped membrane 214 and disk-shaped membrane 210, covering the end of the cylindrical body 212. The toroidal-shaped closed region indicated by 216 contains the acid for bleeding into the adjacent cylindrical chamber. The acid may be in concentrated form alone, or it may be imbedded in some material, such as a gel, for inhibiting the rate of diffusion of the acid through membrane 210. The acid reservoir illustrated in FIG. 4G is presented by way of example only, other particular embodiments are possible, and indeed, may be preferred over the illustrated embodiment for particular applications.

Redox potentials are measured in a manner directly analogous to pH measurements. The only difference is that fluorescent indicator molecules are employed which are sensitive to redox potentials. Such indicator molecules include trianylmethane and triazinyl dyes.

Chloride ions are detected by taking advantage of (1) the high affinity that silver has for chloride (over fluoresceinate), and (2) the quenching effect of silver on fluorescein. In the absence of chloride, the silver remains bound to fluorescein (as silver fluorescinate) and no fluorescent signal is generated in response to illumination. In the presence of chloride, the silver preferentially associates with the chloride, allowing the fluorescein to fluoresce upon illumination. The strength of the fluorescent signal is related to the concentration of chloride exposed to the silver fluoresceinate. The fluoresceinate is held adjacent to the face of the fiber core in the same manner as the above-described fluorescent pH-indicator molecules.

Salt concentrations can be determined by attaching certain water sensitive fluorescent indicator molecules to gels, which in turn are attached to the end of a fiber optic. A gel consists of a cross-linked network of polymers and a liquid medium trapped by the network. The properties of the gel depend strongly on the interaction of these two components. In particular, an aqueous gel will change volume by drawing in or expelling water as various physical parameters of the aqueous environment change, e.g., temperature and salt concentration. Thus, a fluorescent molecule embedded in the gel will be exposed to varying concentrations of water as the gel responds to changes in these parameters. If the fluorescent output of the embedded molecule depends on water concentration, then the combination of the gel and fluorescent molecule provides a method for detecting changes in the physical parameters affecting gel volume.

Many linking means are available for covalently binding dyes to the gel polymers. For example, the two water-dependent dyes, erythrosin and methyl green, can be linked to a gel by cyanogen bromide.

Oxygen can be sensed by immobilizing the dye rose bengal (Eastman Kodak Company, Rochester, NY) adjacent to the end face of a fiber optic core. Rose bengal fluoresces in the absence of oxygen, but phosphoresces in its presence. Thus, with the aid of a phosphorimeter, for example like the one shown in FIG. 6, the presence of oxygen can be sensed.

For medical appliations the above-mentioned probes and adjacent sections of fiber optic must be treated with a clot-inhibiting agent, such as heparin, albumin, or the like.

The foregoing means for sensing specific chemical species are specific examples of generic sensing means, termed optrode means, which is adapted for use with single fiber optics for detecing chemical species. The optrode means comprises an optical transducing means and an immobilization means. The reservoir means used in some of the foregoing examples is taken to be part of the repective immobilization means. Optrode means are attached to fiber optics by connecting means, which includes cement, clamps, or the like. The connecting means may also be integrated with the immobilization means, for example, as with the immobilization means with reservoir means in FIG. 4G. There the cylindrical body 212 is attached to the fiber optic by a closely fitting sleeve, or collar, which may include cement.

The limited travel of the illumination beam in the sample before its spreading renders most of the generated fluorescenece non-collectible by the fiber limits the methods total sensitivity. This can be avoided by containing the beam spread in a glass capillary as illustrated in FIG. 4C. There, the arrangment 44 is whose in combination with a glass capillary 80. Suitable means generally illustrated at 82 are provided by mechanically maintaining the capillary in concentric alignment with arrangement 44.

Figure 5:
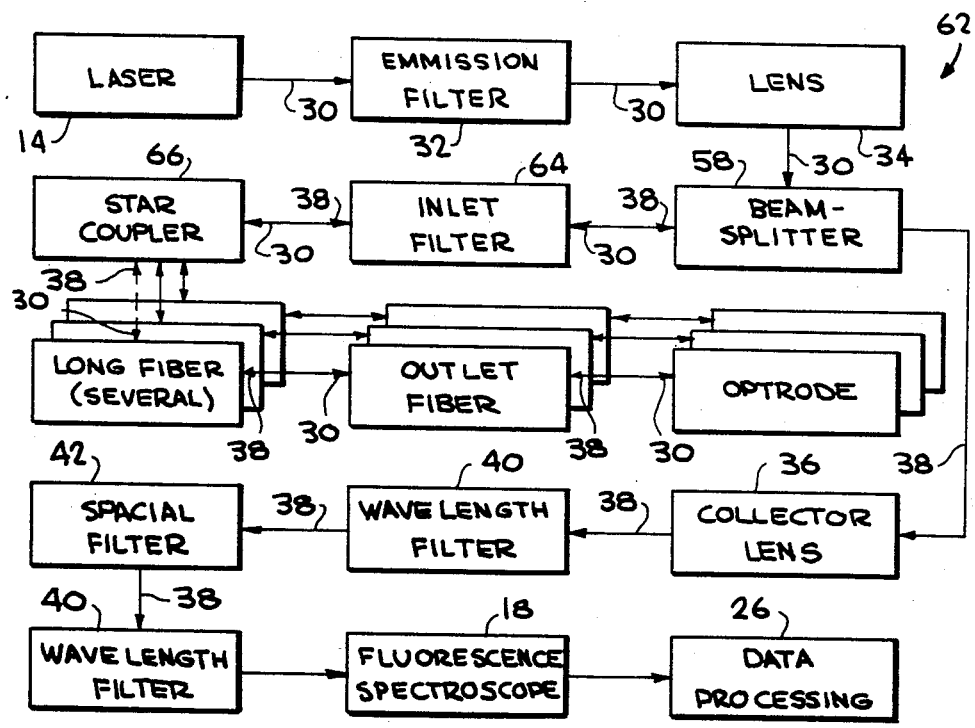
FIG. 5 is a diagrammatic illustration, in block diagram, of a system for obtaining fluorimetric information from one or a number of remote locations (substantially simultaneously) and in accordance with a preferred embodiment of the present invention.

Having described overall information gathering system 10 in detail, it should be apparent that this system has been designed for obtaining specific fluorimetric information at only one location. Because of the relatively high cost of fluorimetric analytic equipment, specifically a fluorescence spectroscope and laser light sources, it would be highly desirable to use a single laser and spectroscope to obtain fluorimetric information from a number of different locations substantially simultaneously, that is, in sufficiently rapid succession to make it unnecessary to physically move the entire equipment to the various locations. The system for achieving this is illustrated in FIG. 5 and is generally indicated at 62. As seen there, the same laser 14 may be brought remotely to the various information bearing locations for producing previously recited beam 30. The same emission filter 32, lens 34 and beam splitter 58 described with respect to FIG. 1 can be provided for the same reasons described thereby.

Figure 3:
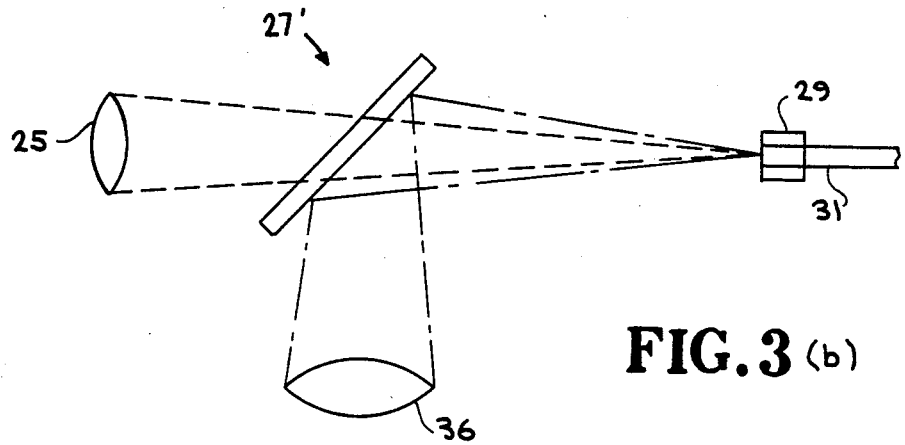
FIG. 3B diagrammatically illustrates a beam splitter arrangement especially suitable for use in the system of FIG. 3A.
FIG. 3C diagrammatically illustrates another beam splitter arrangement suitable for use in the system of FIG. 3A.
Figure 3:
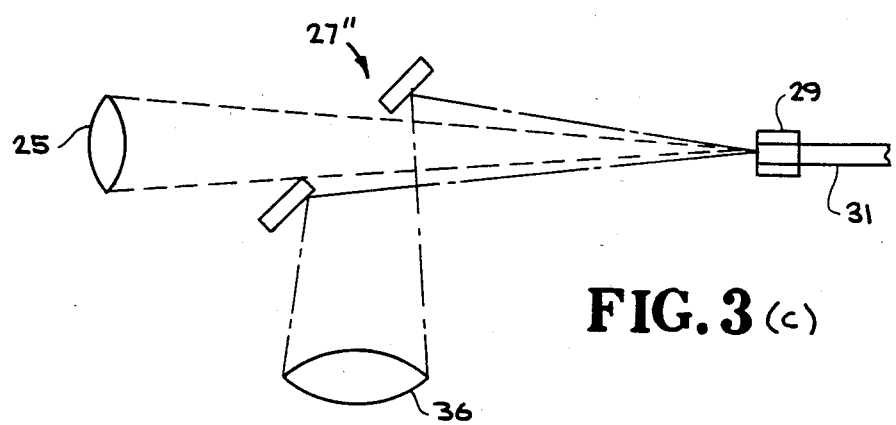

As seen in FIG. 5, beam 30 is applied from the beam splitter to a cooperating end of an inlet optical fiber diagrammatically illustrated at 64. The inlet fiber may be identical in construction to previously described optic fiber 20. While not shown, the beam splitter itself includes an optical lens or like means for focusing beam 30 onto the adjacent end of fiber 64 whereby to assure that the entire beam enters the inlet fiber or the beam splitter may be like those shown in FIGS. 3B and 3C. The opposite end of this fiber is optically coupled, for example, by means of a fiber connector and/or suitable lens, to the input of a star coupler 66. This latter device serves to alternatively direct beam 30 through a number of different outlets utilizing a combination of reflectors (e.g., mirrors) including at least one which is movable between a number of different positions. This movement can take place manually, or automatic means can be readily provided. One such device is manufactured by Math Associates (Math Associates, Inc., Port Washington, NY) under the name of Two Port Optical Coupler. At each outlet of star coupler 66 is one end of a main or primary (long) optical fiber 68 which is coupled to its associated outlet by suitable optical means, for example, a lens, so that beam 30 may be alternatively directed into any one of the longer fibers. Overall system 62 is shown including four primary fibers 68 in FIG. 3 and, therefore, star coupler 66 includes at least four outlets.

All of the components making up overall system 10 thus far described, that is, laser 14, emission filter 32, lens 34, beam splitter 58, inlet fiber 64, star coupler 66 and the coupled ends of primary fibers 68 are preferably located at the same central location. The various primary fibers extend from this location to the various information bearing locations. At each of these latter locations an outlet fiber 70 is optically coupled at one end to the adjacent end of an associated primary fiber by suitable means, for example by an appropriate lens such that the beam 30 travelling through the primary fiber enters the outlet fiber. The other end of each outlet fiber includes what is referred to as an optrode for bringing its associated incoming beam 30 onto a corresponding material 22 and for collecting the light from the fluorescent display resulting therefrom. Outlet fibers 70 can be constructed in he same manner as previously described optical fibers 20 and the optrodes can be identical to and connected in the same manner as previously described focusing/collection arrangement 44 or the other arrangements shown in FIG. 4.

The light collected by each optrode 44 in system 62 produces a corresponding outgoing beam 38, as in system 10. Each of these latter beams passes through outlet fiber 70 in the opposite direction as beam 30 and thereafter through its associated primary fiber 68, again the opposite direction as beam 30. The various beams 38 are thereafter alternatively directed into star coupler 66 (through associated outlets of the latter) and from the star coupler into the single inlet fiber 64 towards beam splitter 58. After leaving inlet fiber 64 in the opposite direction as beam 30, beam 38 is directed through beam splitter 58 to a collector lens 36 which may be identical to the previously described collector lens comprising part of system 10. From the collector lens, the beam passes through a wavelength filter 40 and spatial filter 42 as in system 10 and, if desired, still another wavelength filter 40 and finally into spectroscope 18. The information from the spectroscope may be applied to appropriate data processing equipment 26 as in system 10.

From the foregoing, it should be apparent that a number of different remote locations which may or may not be in hostile environments can be substantially simultaneously monitored for fluorimetric information using a single laser and only one fluorescence spectroscope which are generally the most expensive components making up the overall system. In fact, in system 62, the only duplication of components associated with the various information bearing locations are the primary fibers, outlet fibers and optrodes.

It should also be apparent that this multi-position technique is equally applicable for obtaining from various different locations information other than fluorimetric information. More specifically, a system similar to system 62 could be provided for monitoring temperature or other types of information which can be obtained optically, that is, by means of an incoming beam and an outgoing beam. For example, in the case of temperature, the incoming beam is passed into the area being monitored through an appropriate sensor such as the one described in U.S. Pat. No. 4,179,927. The outgoing beam is characteristic of the temperature at the sensor, as described in the patent just recited. In other words, the incoming beam in combination with the sensor would provide a signal in the sensor (e.g., the incoming beam itself) and this signal by means of reflection forms the basis for an outgoing beam directed back out of the sensor and towards its associated detector as described in the U.S. Pat. No. 4,179,927. This is only one possible information gathering approach which could be used in lieu of or in combination with the gathering of fluorimetric information in overall system 62. In the case of temperature sensing or similar situations wherein the incoming and outgoing beams may have common wavelengths, it may in special cases be necessary to use separate optical networks for carrying the incoming and outgoing beams to reduce the background. However, the same laser and detector system could be readily provided as in system 62.

The descriptions of the foregoing embodiments of the invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. An apparatus for monitoring the salt concentration of an associated fluid and for generating a fluorescent signal related to said salt concentration, the apparatus comprising:

a fiber optic through which an illumination beam from an associated light source is transmitted from a first end of the fiber optic to a second end of the fiber optic;

a plurality of water-sensitive fluorescent indicator molecules;

a gel in contact with the associated fluid, the gel having a volume which is responsive to changes in the salt concentration of the associated fluid, and the gel holding the plurality of water-sensitive fluorescent indicator molecules adjacent to the second end of the fiber optic such that light from the illumination beam leaving the second end of the fiber optic illuminates the plurality of water-sensitive fluorescent indicator molecules and such that a portion of the fluorescent emissions generated by the plurality of water-sensitive fluorescent indicator molecules is collected by the second end of the fiber optic and transmitted to the first end of the fiber optic, the transmitted fluorescent emissions forming a fluorescent signal; and detection means associated with the first end of the fiber optic for separating the fluorescent signal from the illumination beam and for relating the intensity of the fluorescent signal to the salt concentration of the associated fluid.

2. The apparatus as recited in claim 1 wherein said plurality of water-sensitive fluorescent indicator molecules includes molecules of methyl green.

3. The apparatus as recited in claim 1 wherein said plurality of water-sensitive fluorescent indicator molecules includes molecules of erythrosin.

4. An apparatus for monitoring the presence of chloride ions in an associated fluid and for generating a fluorescent signal related to chloride ion concentration therein, the apparatus comprising:

a fiber optic through which an illumination beam from an associated light source is transmitted from a first end of the fiber to a second end of the fiber optic;

a plurality of silver fluoresceinate molecules, the silver fluoresceinate molecules each having a silver moiety and a fluoresceinate moiety;

immobilization means for holding the fluoresceinate moieties of the plurality of silver fluoresceinate molecules adjacent to the second end of the fiber optic and in contact with the associated fluid such that light from the illumination beam leaving the second end of the fiber optic illuminates the fluoresceinate moieties of the plurality of silver fluoresceinate molecules, and such that a portion of the fluorescent emissions generated by the fluoresceinate moieties is collected by the second end of the fiber optic and transmitted to the first end of the fiber optic; and detection means associated with the first end of the fiber optic for separating the fluorescent emissions transmitted to the first end of the fiber optic from the illumination beam and for relating the intensity of the fluorescent emissions to the chloride ion concentration of the associated fluid.

5. An apparatus for monitoring the presence of ferric ions in an associated fluid and for generating a fluorescent signal related to ferric ion concentration therein, the apparatus comprising:

a fiber optic through which an illumination beam is transmitted from a first end of the fiber optic to a second end of the fiber optic;

immobilization means in contact with the associated fluid, the immobilization means having a first membranous-walled chamber whose interior receives light from the illumination beam emanating from the second end of the fiber optic, the first membranous-walled chamber being permeable to uranyl ions and ferric ions and containing a known concentration of polyphosphoric acid;

reservoir means having a second membranous-walled chamber for holding uranyl ions, the second membranous-walled chamber communicating with the first membranous-walled chamber through a uranyl ion-permeable membrane such that uranyl ions from the second membranous-walled chamber continously diffuse into the first membranous-walled chamber such that the uranyl ions are illuminated by the illumination beam and are caused to generate fluorescent emissions, the fluorescent emissions is being modulated by the presence of ferric ions in a concentration-dependent manner, and such that a portion of the generated fluorescence is collected by the second end of the fiber optic and transmitted to the first end of the fiber optic, the transmitted portion of the fluorescent emissions forming a fluorescent signal; and detection means associated with the first end of the fiber optic for separating the fluorescent signal from the illumination beam and for relating the fluorescent signal to the ferric ion concentration of the associated fluid.

6. The apparatus of claim 5 wherein said fluorescent signal is fluorescent lifetime of said uranyl ions, said illumination beam intermittantly illuminates said uranyl ions in said first membranous-walled chamber, and said detection means includes means for measuring fluorescence lifetime.

* * * * *

UNITED STATES PATENT OFFICE
CERTIFICATE OF CORRECTION

Patent No. 4,577,109　　　　　　　　　Dated　March 18, 1986

Inventor(s)　　Tomas B. Hirschfeld (Deceased)

It is certified that error appears in the above-identified patent and that said Letters Patent are hereby corrected as shown below:
Column 1, line 4, the following should be inserted.

-- The Government has rights in this invention pursuant to Contract

No. W-7405-ENG-48 awarded by the U.S. Department of Energy. --

Signed and Sealed this

Twenty-second Day of March, 1988

Attest:

DONALD J. QUIGG

*Attesting Officer*　　　　*Commissioner of Patents and Trademarks*